United States Patent [19]
Fujimoto

[11] Patent Number: 5,643,179
[45] Date of Patent: Jul. 1, 1997

[54] METHOD AND APPARATUS FOR ULTRASONIC MEDICAL TREATMENT WITH OPTIMUM ULTRASONIC IRRADIATION CONTROL

[75] Inventor: Katsuhiko Fujimoto, Kanagawa-ken, Japan

[73] Assignee: Kabushiki Kaisha Toshiba, Kawasaki, Japan

[21] Appl. No.: 365,149

[22] Filed: Dec. 28, 1994

[30] Foreign Application Priority Data

Dec. 28, 1993 [JP] Japan .................. 5-336806

[51] Int. Cl.$^6$ ...................... A61B 8/00
[52] U.S. Cl. ............... 601/2; 128/660.03; 601/3
[58] Field of Search ............ 128/660.03; 601/2, 601/3, 4; 607/97

[56] References Cited

U.S. PATENT DOCUMENTS

| Re. 33,590 | 5/1991 | Dory | 128/660.03 |
|---|---|---|---|
| 4,658,828 | 4/1987 | Dory | 128/660 |
| 5,080,101 | 1/1992 | Dory | 128/660.03 |
| 5,080,102 | 1/1992 | Dory | 128/660.03 |
| 5,111,822 | 5/1992 | Dory | 128/660.03 |
| 5,143,073 | 9/1992 | Dory | 128/660.03 |
| 5,150,711 | 9/1992 | Dory | 128/660.03 |
| 5,150,712 | 9/1992 | Dory | 128/660.03 |

FOREIGN PATENT DOCUMENTS

| 0 162 753 | 11/1985 | European Pat. Off. . |
|---|---|---|
| 0 170 416 | 2/1986 | European Pat. Off. . |
| 2 113 099 | 8/1983 | United Kingdom . |

*Primary Examiner*—Marvin M. Lateef
*Assistant Examiner*—Eleni Mantis Mercader
*Attorney, Agent, or Firm*—Foley & Lardner

[57] ABSTRACT

An ultrasonic medical treatment scheme for optimally controlling the irradiation energy of the intense ultrasonic waves. In this scheme, an ultrasonic energy of the ultrasonic waves irradiated at a tissue boundary surface such as a body surface is obtained, and at least one of the driving power and the irradiation time of the ultrasonic wave generation source in the applicator is controlled such that the ultrasonic energy at the tissue boundary surface becomes less than a prescribed threshold which is determined in view of an influence on the tissue boundary surface due to the ultrasonic waves. In addition, the ultrasonic energy of the ultrasonic waves irradiated at a focal point of the ultrasonic waves can also be obtained and the applicator can be controlled such that the ultrasonic energy at the focal point becomes greater than another prescribed threshold determined in view of a medical treatment effect at the focal point due to the ultrasonic waves at the same time.

20 Claims, 5 Drawing Sheets

METHOD AND APPARATUS FOR ULTRASONIC MEDICAL TREATMENT WITH OPTIMUM ULTRASONIC IRRADIATION CONTROL

BACKGROUND OF THE INVENTION

1. Field of the Invention

The present invention relates to an ultrasonic medical treatment apparatus for applying a medical treatment to a tumor and the like within a living body by using ultrasonic waves.

2. Description of the Background Art

In recent years, a type of medical treatment called MIT (Minimum Invasive Treatment) has been attracting attentions in various fields of the medicine.

One example of this MIT is a lithotriptor apparatus for applying a lithotripsy treatment to a calculus non-invasively, which has revolutionized medical treatment of the urological calculus. For this lithotriptor apparatus, many different types of the intense ultrasonic wave generation source are available, including an underwater discharge type, an electromagnetic induction type, a micro-explosion type, and a piezoelectric type. Among these, the piezoelectric type has many advantageous features such as that the focal point is small, that no articles of consumption is required, that the pressure of the intense ultrasonic waves can be controlled freely, and that the focal point position can be controlled freely by a phase control of driving voltages to be applied to a plurality of piezoelectric transducer elements, in spite of a drawback that the pressure of the intense ultrasonic waves is rather small. (See Japanese Patent Application Laid Open No. 60-145131 and U.S. Pat. No. 4,526,168 for further details.)

On the other hand, this MIT is also attracting attentions in the field of the cancer treatment. In particular, in a case of a cancer, its medical treatment is still largely relying on the surgical operations today and there are many incidences of severely damaging an original function and/or an outward appearance of an organ with a cancer, such that a heavy burden would be left on the patient even if it is possible to prolong a life of a patient. In view of such current situations, there are strong demands in this field for a development of less invasive medical treatment method and apparatus taking the QOL (Quality Of Life) into account properly.

In such a recent trend, the so called hyperthermia treatment method has been attracting large attentions as a method of medical treatment of a malignant tumor, i.e. a cancer. This hyperthermia treatment method is a medical treatment method in which cancer cells are selectively killed by warming and maintaining a diseased portion at a temperature over 42.5° C., utilizing different heat sensitivities of tumor tissues and normal tissues. As for a scheme of warming, a scheme using the electromagnetic waves such as microwaves has been developed first, but in this scheme, it is difficult to warm a tumor at a deep part of a body selectively due to the electrical property of the living body, so that the satisfactory medical treatment result cannot be expected for a tumor at a part deeper than 5 cm. For this reason, for a treatment of a tumor at a deep part, a warming scheme using the ultrasonic energy having superior focusing and depth transmission properties has been proposed (Japanese Patent Application Laid Open No. 61-13955).

There has also been a report of a medical treatment method in which the above described hyperthermia treatment method is further developed to heat a tumor portion at a temperature over 80° C. by focusing the ultrasonic waves generated by the piezoelectric transducer elements to a diseased portion so as to kill the tumor tissues instantaneously by causing the thermal degeneration (G. Vallancien et al., Progress in Urology, Vol. 1, pp. 84–88, 1991).

In this type of the medical treatment method, unlike the conventional hyperthermia treatment, there is a need to irradiate the ultrasonic waves thoroughly by scanning the focal point over the entire region in which the tumor exists, because very intense ultrasonic waves are going to be injected into a very localized region in a vicinity of the focal point. In particular, in a case of irradiating the ultrasonic waves as intense as several thousand W/cm$^2$, the change of the acoustic characteristic due to the cavitation or the thermal degeneration of the diseased portion produced in conjunction with the ultrasonic wave irradiation is expected to pose a serious problem, and can possibly be a cause of the undesirable side effect, but the method of intense ultrasonic wave irradiation for resolving this problem has already been proposed by the present inventor and others (Japanese Patent Application No. 4-43604).

However, this type of the medical treatment method still has a drawback in that, as a very high energy is to be concentrated in a localized region, there is a possibility for causing the side effect such as a degeneration due to heat generation and a mechanical destruction of tissues when the acoustic characteristic changes at a tissue boundary surface of an organ or the like located in the ultrasonic wave passing region. This is particularly prominent at a coupling surface of an acoustic coupling agent of the ultrasonic wave generation source and a body surface of the living body, and in addition, the acoustic characteristics of the skin and the internal tissues are also expected to be different, so that there is a possibility for the side effect such as a burning to be caused on the organ in the ultrasonic wave passing region or the body surface by the intense ultrasonic wave irradiation. In fact, the degeneration of the body surface due to the ultrasonic wave irradiation over an extended period of time had been confirmed in an animal experiment conducted by the present inventor and others.

Consequently, there appears to be a need for optimally controlling the irradiation intensity and time of the intense ultrasonic waves at the tissue boundary surface, but such an optimum control scheme has not been available heretofore.

SUMMARY OF THE INVENTION

It is therefore an object of the present invention to provide a method and an apparatus for the ultrasonic medical treatment capable of optimally controlling the irradiation intensity and time of the intense ultrasonic waves.

According to one aspect of the present invention there is provided an ultrasonic medical treatment apparatus, comprising: applicator having an ultrasonic wave generation source for irradiating ultrasonic waves to a treatment target portion within a body to be examined; energy obtaining means for obtaining an ultrasonic energy of the ultrasonic waves irradiated at a tissue boundary surface of the body to be examined; and control means for controlling the applicator such that the ultrasonic energy at the tissue boundary surface obtained by the energy obtaining means becomes less than a prescribed threshold. The control means may also control the applicator such that the ultrasonic energy at the focal point obtained by the energy obtaining means becomes greater than another prescribed threshold.

According to another aspect of the present invention there is provided a method of ultrasonic medical treatment, comprising the steps of: irradiating ultrasonic waves from an applicator having an ultrasonic wave generation source to a treatment target portion within a body to be examined; obtaining an ultrasonic energy of the ultrasonic waves irradiated at a tissue boundary surface of the body to be examined; and controlling the applicator such that the ultrasonic energy at the tissue boundary surface obtained at the obtaining step becomes less than a prescribed threshold.

Other features and advantages of the present invention will become apparent from the following description taken in conjunction with the accompanying drawings.

DETAILED DESCRIPTION OF THE PREFERRED EMBODIMENTS

Figure 1:
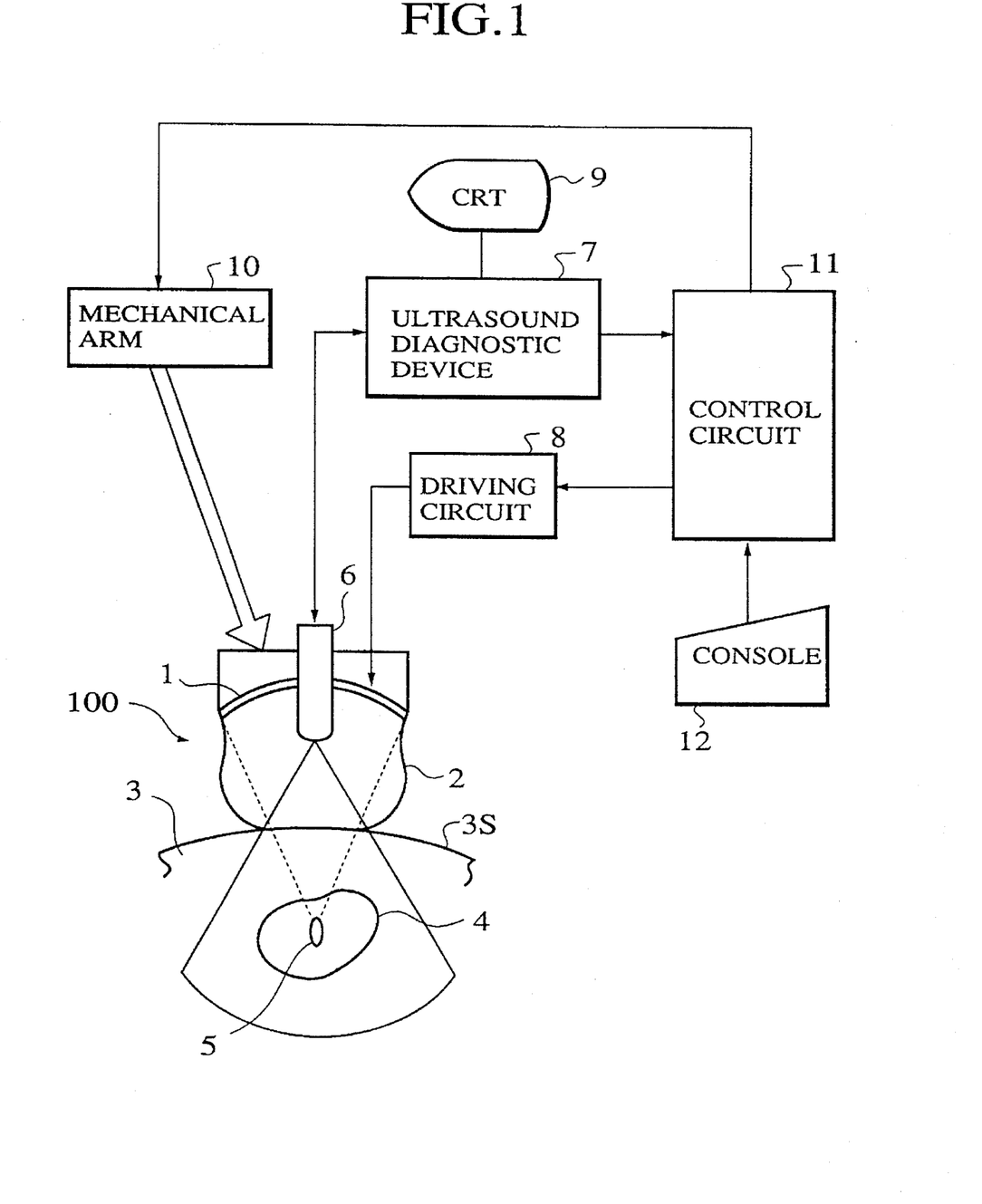
FIG. 1 is a schematic block diagram of one embodiment of an ultrasonic medical treatment apparatus according to the present invention.

Referring now to FIG. 1, one embodiment of a method and an apparatus for the ultrasonic medical treatment according to the present invention will be described in detail.

In this embodiment, the apparatus has a configuration as shown in FIG. 1, in which an applicator 100 comprises a piezoelectric element group 1 formed by one or a plurality of piezoelectric transducer elements for irradiating intense treatment ultrasonic waves, and a water bag 2 filled with a coupling fluid for leading the intense ultrasonic waves from the piezoelectric element group 1. At a time of the medical treatment, the applicator 100 is mounted on a body surface 3S of the patient 3, with an ultrasonic jelly (not shown) applied between the water bag 2 and a skin of the body surface 3S to secure the contact. Then, after a focal point 5 of the intense ultrasonic waves is set on a diseased portion 4 within the patient 3, the driving circuit 8 drives the piezoelectric element group 1 to irradiate the intense ultrasonic waves toward the focal point 5. The applicator 100 itself can be moved by a mechanical arm 10 under a control of a control circuit 11 according to data entered by an operator through a console 12.

In addition, it is also possible to set up a desired medical treatment range on the image of the diseased portion 4 obtained in advance, and scan and treat this medical treatment range according to a prescribed procedure. To this end, at a center of the piezoelectric element group 1, the applicator 100 is further equipped with an ultrasound probe 6 for transmitting and receiving imaging ultrasonic waves, according to which ultrasound images are reconstructed as the B mode images by an ultrasound diagnostic device 7 and displayed on a CRT 9.

In the embodiment of FIG. 1, the energy obtaining means is comprised of the ultrasound diagnostic device 7 and control circuit 11. The depth of the focal point 5 with respect to the body surface 3S is measured by using the ultrasound diagnostic device 7. This measurement is used by the control circuit 11 to calculate the ultrasound energy irradiated at the tissue boundary surface and at the focal point while the focal point 5 is scanned over the entire diseased portion 4 thoroughly.

In this configuration of FIG. 1, the control circuit 11 carries out the optimum control of the ultrasonic wave irradiation time as follows.

First, at a time of the initial positioning, a position of the focal point 5 in a depth direction from the body surface 3S is measured by using the ultrasound diagnostic image displayed on the CRT 9, and that position is specified as a reference point from the console 12. Then, at a time of irradiating the intense ultrasonic waves while scanning the focal point 5 thoroughly over the entire diseased portion 4 by controlling the mechanical arm 10 from the control circuit 11, as the depth of the focal point 5 varies depending on the position of the focal point 5, the irradiation is carried out while controlling the driving time of the driving circuit 8 from the control circuit 11 according to the depth of the focal point 5.

Here, the optimum driving time is determined as follows.

According to the result of the experiment conducted by the present inventor and others, it is known that, for the constant frequency (f=1.65 [MHz]), the burning (thermal degeneration) at the body surface 3S depends on the ultrasonic energy density $W_S$ (=ultrasonic wave intensity $I_S \times$ irradiation time $T_S$) at the body surface 3S. Namely, with the ultrasonic wave intensity $I_S$=25 [W/cm$^2$] at the body surface 3S, the thermal degeneration was caused at the body surface 3S when the irradiation time t exceeded 3 seconds for instance, so that it can be deduced that the degeneration will not be caused as long as the energy density $W_S$ at the body surface 3S is less than 75 [J/cm$^2$] for the frequency f=1.65 [MHz].

The burning at the body surface 3S is caused by the difference in the acoustic characteristic between the skin and the coupling fluid or the internal tissues, and the attenuation due to the skin tissue can be considered as proportional to the frequency f, so that the level of degeneration at the body surface 3S depends on a product of the ultrasonic energy density $W_S$ and the frequency f, and it can be deduced that the burning (thermal degeneration) at the body surface 3S will not be caused by the continuous ultrasonic waves irradiation for a period of time less than or equal to $t_S$ satisfying the following equation (1).

$$W_S \times f = I_S \times t_S \times f < 124 \text{ [MHz·J/cm}^2\text{]} \qquad (1)$$

Figure 2A:
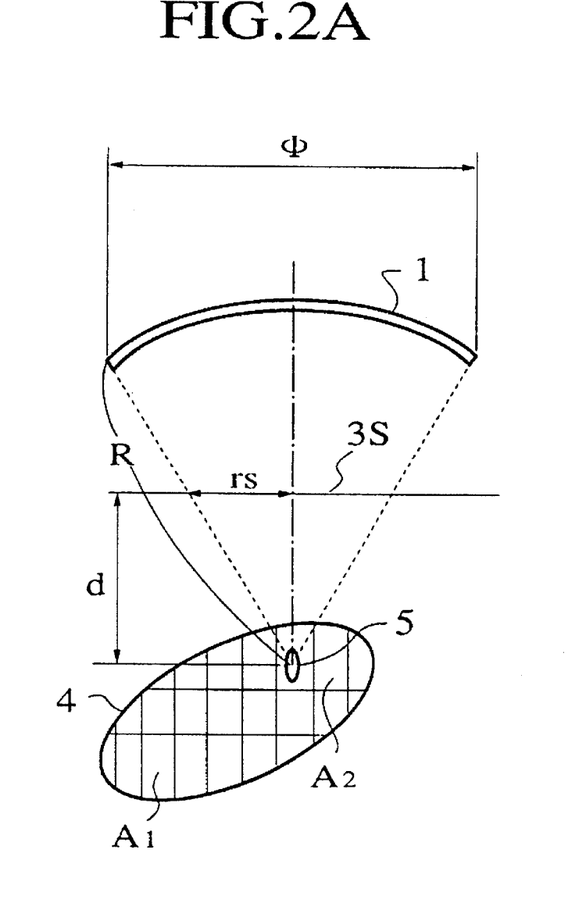
FIGS. 2A and 2B are diagrams for explaining a determination of an upper limit for the ultrasonic wave irradiation time in the apparatus of FIG. 1.

Here, as shown in FIG. 2A, when the opening diameter of the piezoelectric element group 1 is $\phi$ [cm], the focal point distance is R [cm], the focal point depth from the body surface 3S is d [cm], and the piezoelectric transducer element of the electro-acoustic conversion efficiency k is to be driven by a power P [W] which is entered in the piezoelectric transducer element, the ultrasonic wave intensity $I_S$ at the body surface 3S can be expressed by the following equation (2).

$$I_S = Pk/S \qquad (2)$$

where $S = \pi r_S^2$ is a body surface passing area through which the ultrasonic waves pass at the body surface 3S, and a body surface passing area radius $r_S$ is given by the following equation (3).

$$r_S = d \cdot \phi/2\{R^2 - (\phi/2)^2\}^{1/2} \qquad (3)$$

Figure 2B:
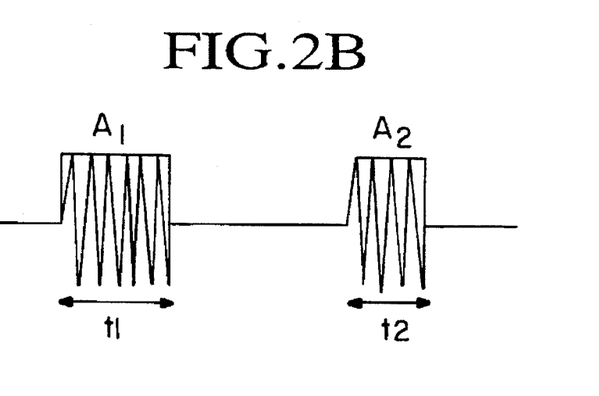

Thus, it is possible to obtain the time t for which the intense ultrasonic wave irradiation can be made without causing the burning at the body surface 3S according to the above equations (1) to (3). For example, as indicated in FIG. 2B, the optimum irradiation time for the intense ultrasonic waves can be determined to be a longer time $t_1$ for a deeper portion $A_1$ of the diseased portion 4 and a shorter time $t_2$ for a shallower portion $A_2$.

On the other hand, there is also a condition required for killing the cells of the diseased portion 4, which is determined as follows.

According to the result of the experiment conducted by the present inventor and others, for the frequency f=1.65 [MHz], the temperature rise of approximately 11.5° C. was obtained by the irradiation with the focal point peak ultrasonic wave intensity $I_P$=450 [W/cm²] for the irradiation time $t_P$=1 second for instance, so that it can be deduced that, in order to obtain the temperature rise of over $\Delta T°$ C. at the focal point 5, it is necessary to satisfy the following equation (4).

$$I_P \times t_P \times f > 64 \; [J \cdot MHz/cm^2/°C.] \times \Delta T \qquad (4)$$

Now, speaking from a viewpoint of the heat generation and the medical treatment effect at the focal point, it can be said that most cells can be killed within several seconds (typically 3 to 6 seconds) by the heating at a temperature over 60° C. according to the Arrhenius' equation (a formula for a change of reaction speed for the protein denaturation and the enzyme inactivation due to temperature) and the survival rate curve of a treatment target cell with respect to the protein denaturation and the enzyme inactivation.

Then, in order to heat the deep part of the body at a temperature over 60° C. for instance, assuming the body temperature to be approximately 35° C., the temperature rise of over 25° C. is necessary so that, according to the above equation (4), it is necessary to satisfy the following equation (5).

$$I_P \times t_P \times f > 64 \times 25 = 1600 \; [J \cdot MHz/cm^2] \qquad (5)$$

Moreover, in order to heat at a temperature over 85° C. for which the living body tissue can be killed instantaneously by the thermal degeneration, the temperature rise of over 50° C. is necessary so that it is necessary to satisfy the following equation (6).

$$I_P \times t_P \times f > 64 \times 50 = 3200 \; [J \cdot MHz/cm^2] \qquad (6)$$

In other words, in order to kill the living body tissue by the thermal degeneration in 1 second with the frequency f=1.5 [MHz], it is necessary to have the focal point peak ultrasonic wave intensity $I_P$ of over 2133 [W/cm²], which is nearly in agreement with the result of the experiment conducted by the present inventor and others.

Here, the focal point ultrasonic wave intensity in a non-attenuative medium depends on the focusing level (i.e., the opening diameter $\phi$ [cm] and the focal point distance R [cm]) and the frequency f [MHz] of the ultrasonic waves, as indicated in the following equations (7) to (9).

Focal point peak intensity [W/cm²]

$$I_P' = 4.37 \cdot Iavg \qquad (7)$$

Average focal point intensity [W/cm²]

$$Iavg = (P_k/\pi r^2) \cdot (84/100)[\%] \qquad (8)$$

First nodal focal point radius [cm]

$$r = 1.2 \cdot C \times 10^2 \cdot R/f \times 10^6 \cdot \phi \qquad (9)$$

where P[W] is the power entered in the piezoelectric transducer element, k is the electro-acoustic conversion efficiency of the piezoelectric transducer element, and C is a sonic speed in the water ($\approx$1500 m/s).

On the other hand, the living body tissue is an attenuative medium with an attenuation rate $\alpha$ of about $-0.5$ [dB/MHz/cm], so that when the focal point 5 of the intense ultrasonic waves is at a depth of d [cm] from the body surface 3S, the focal point peak ultrasonic wave intensity $I_P$ within the living body is given by:

$$10 \times \log_{10}(I_P/I_P') = \alpha \times f \times d \qquad (10)$$

from which it can be expressed as:

$$I_P = I_P' \times 10^{\alpha f d/10} \qquad (11)$$

that is, the ultrasonic wave intensity is attenuated to about ½ at the focal point depth of 3.5 cm.

When a value obtained from this equation (11) which accounts for the attenuation part is substituted into $I_P$ of the above equation (4), it is possible to determine the necessary irradiation time from the shape of the piezoelectric transducer element and the driving frequency and power.

Figure 3:
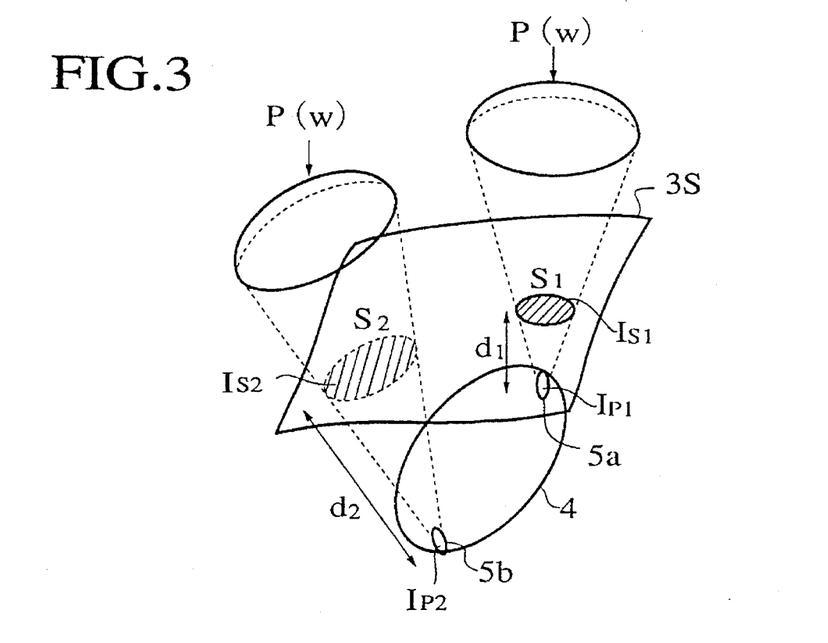
FIG. 3 is a diagram for explaining a determination of a lower limit for the ultrasonic wave irradiation time in the apparatus of FIG. 1.
Figure 4A:
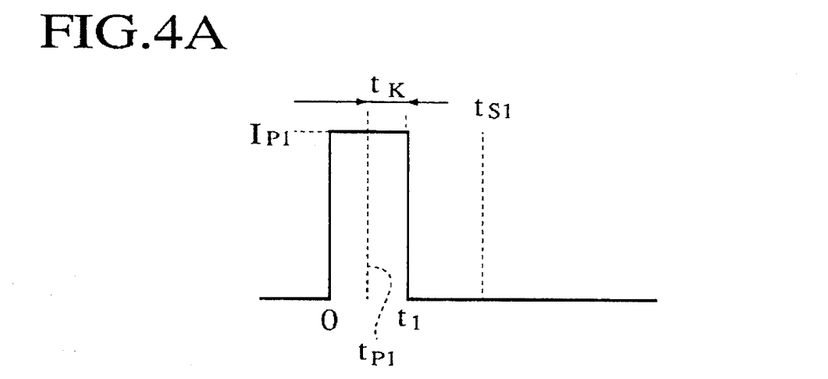
FIGS. 4A and 4B are diagrams of the ultrasonic wave irradiation time and power for two focal point positions shown in FIG. 3.
Figure 4B:
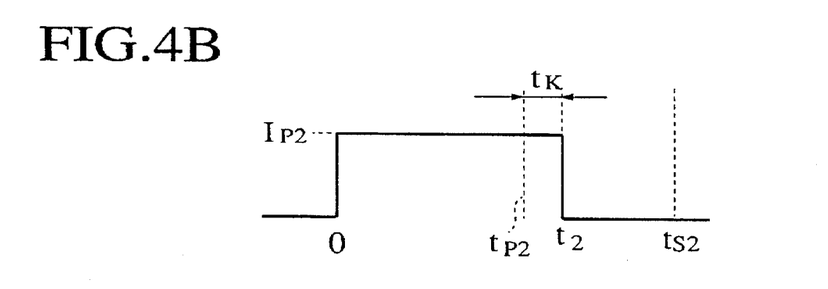
Figure 5A:
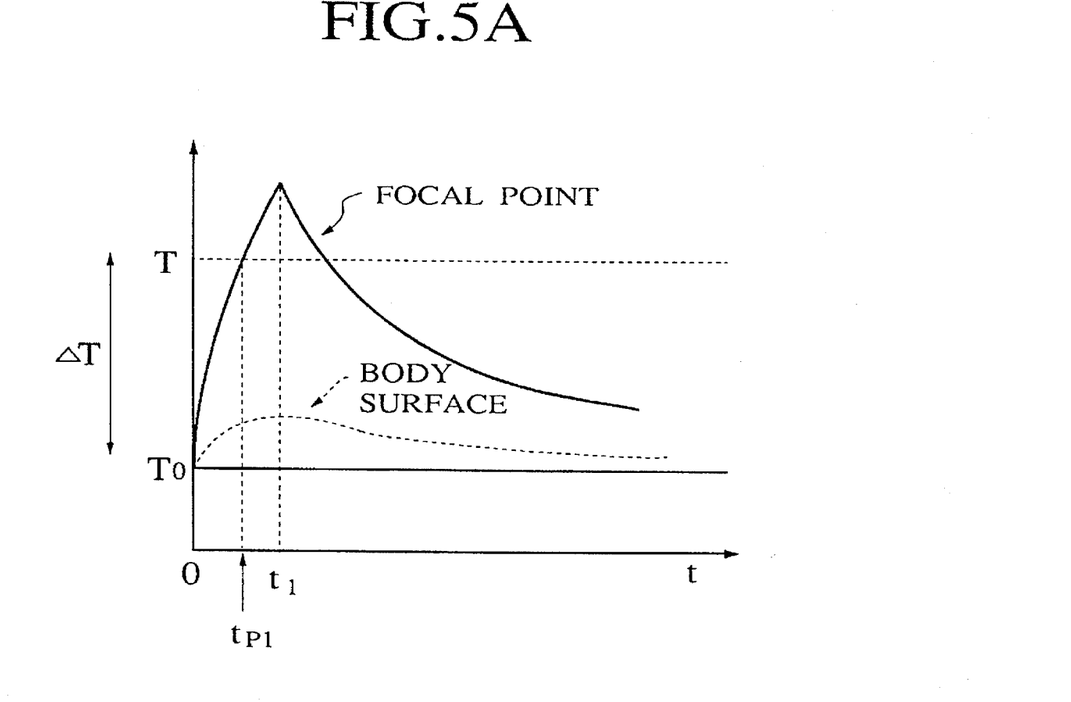
FIGS. 5A and 5B are graphs of temperature rise for cases of FIGS. 4A and 4B.
Figure 5B:
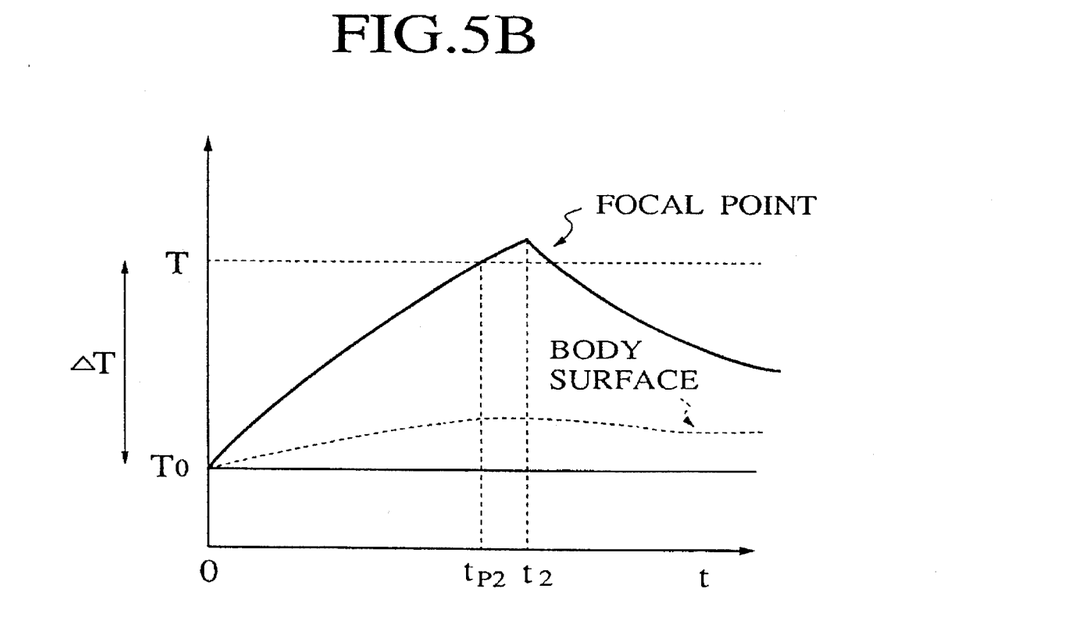

For example, for a focal point 5a at a lesser distance from the body surface 3S and a focal point 5b at a greater distance from the body surface 3S as indicated in FIG. 3, the intensity and the irradiation time of the ultrasonic waves to be irradiated can be determined as shown in FIGS. 4A and 4B, respectively, and the temperatures at the focal point 5a or 5b and the body surface 3S are going to change as indicated in FIGS. 5A and 5B, respectively. In FIGS. 4A and 4B, a time $t_k$ indicates a time determined from the Arrhenius' equation and the survival rate curve which indicates a sufficient time for heating at a temperature T or above in order to kill the cells.

Thus, when the focusing level, the frequency, and the power of the ultrasonic waves are determined, the focal point peak ultrasonic wave intensity $I_P$ can be determined, and the minimum irradiation time $t_P$ required for obtaining the temperature rise of T° C. at the focal point 5 and the maximum irradiation time $t_S$ required for not causing the burning (thermal degeneration) at the body surface 3S can be obtained from the above equations (1) and (4). Here, the focusing level and the driving frequency of the piezoelectric transducer element and the focal point depth at a time of mounting the applicator 100 on the body surface 3S should preferably be determined such that $t_P < t_S$.

Furthermore, it is preferable to determine these values within such ranges that the burst time $t_B$ (=irradiation time of one irradiation) satisfies the following relationship.

$$t_P < t_B < t_S \qquad (12)$$

Here, in order to set the irradiation time as short as possible, the intense ultrasonic waves are irradiated only for the minimum irradiation time $t_P$ plus the time $t_k$ for maintaining the target temperature which is determined by the Arrhenius' equation, as indicated in FIGS. 4A and 4B.

This optimum irradiation time varies according to the depth of the focal point position when the focal point 5 is scanned over the entire diseased portion 4 thoroughly, so that it is calculated and controlled at the control circuit 11 every time the focal point position is changed. Else, it is also possible to set up the irradiation plan according to the shape of the diseased portion 4 at a time of the initial positioning, store the optimum irradiation time pre-calculated for each planned irradiation position in a memory (not shown), and carry out the medical treatment according to the stored values.

As described, according to this embodiment, it is possible to provide a method and an apparatus for the ultrasonic medical treatment capable of optimally controlling the irradiation time of the intense ultrasonic waves so as to achieve the sufficient medical treatment effect at the diseased portion while preventing the damaging (side effect) such as the burning at the body surface.

It is to be noted here that the essence of the present invention lies in the optimum control of the ultrasonic energy to be irradiated to a tissue boundary surface such as a body surface of a body to be examined where the acoustic impedance changes within the ultrasonic wave passing region, so that instead of controlling the irradiation time as described in the above embodiment, it is also possible to control the focal point ultrasonic wave intensity, i.e., the driving power, for the predetermined irradiation time according to the above equations (1) and (4).

Also, instead of the simple proportionality calculation of the ultrasonic wave intensity $I_S$ at the body surface according to the focusing level (i.e., the opening diameter $\phi$ and the focal point distance R) and the focal point depth as in the embodiment described above, it is also possible to actually measure the amount of irradiated ultrasonic energy at that tissue boundary surface by using a suitable measurement device.

Similarly, it is also possible to obtain the ultrasonic wave intensity $I_S$ at the body surface accurately by a simulation in which spherical waves that can be irradiated from a plurality of acoustic points assumed to be arranged at equal intervals on a spherical shell surface of the piezoelectric transducer are superimposed along time axis or frequency axis to simulate the actual ultrasonic wave irradiation, for example.

Figures 6, 7, 8, 9:
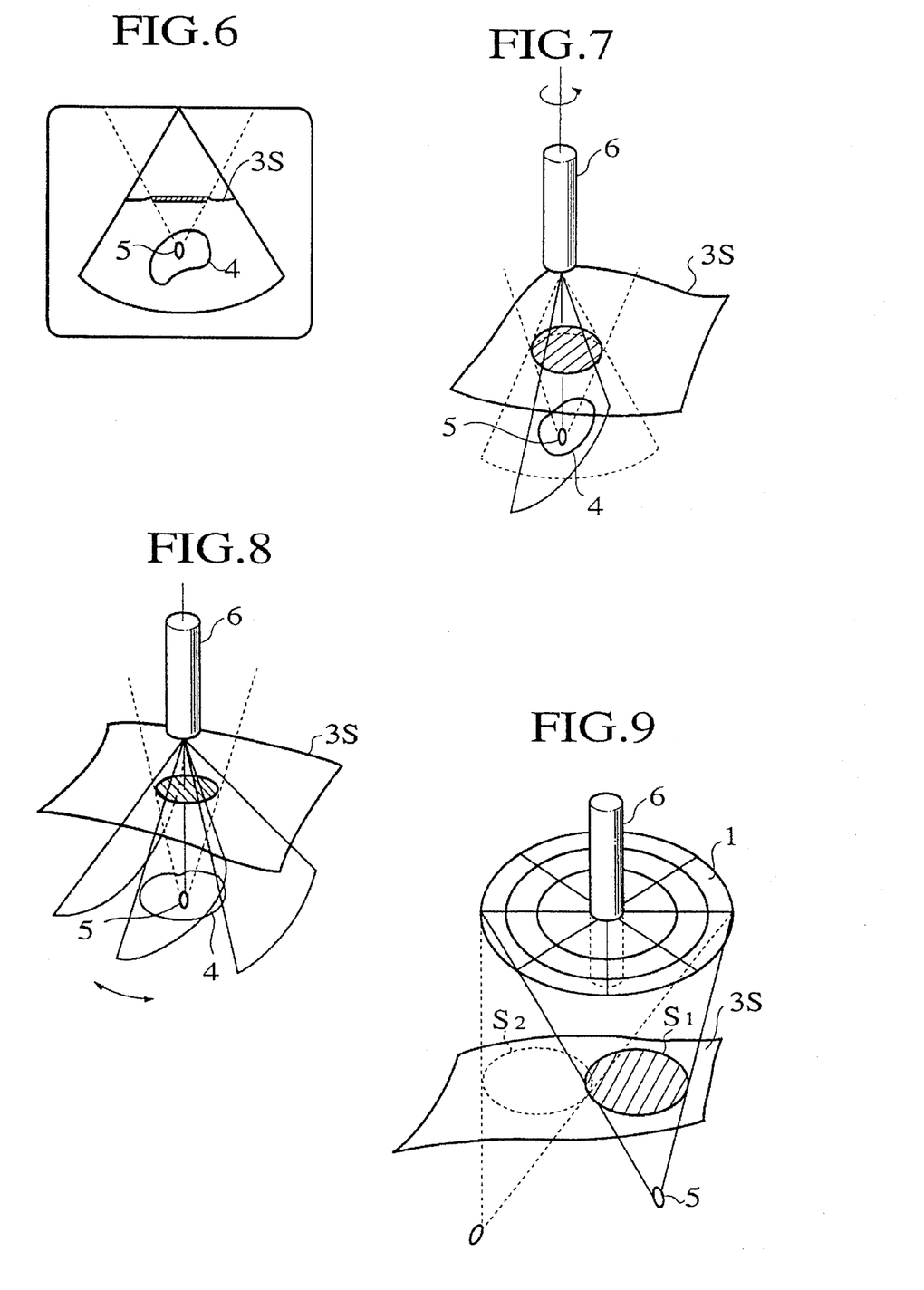
FIG. 6 is an illustration of an ultrasound image display for explaining one possible manner of specifying a boundary surface in the apparatus of FIG. 1.
FIG. 7 is a diagram for explaining one possible manner of operating an ultrasound probe in the apparatus of FIG. 1 for obtaining a body surface passing area.
FIG. 8 is a diagram for explaining another possible manner of operating an ultrasound probe in the apparatus of FIG. 1 for obtaining a body surface passing area.
FIG. 9 is a diagram of piezoelectric transducer elements in a phased array configuration for explaining one possible modification in the apparatus of FIG. 1.

Moreover, the boundary surface of the body surface and the coupling fluid can be recognized on the ultrasound image as a high echo region, so that it is also possible to specify the boundary surface recognized on the ultrasound image by an auxiliary input device such as a light pen on the displayed ultrasound image, as indicated in FIG. 6, or to apply an image recognition for extracting the boundary surface closest to the ultrasound probe 6 by using an appropriate reflection wave threshold. In these cases, by rotating the ultrasound probe 6 as shown in FIG. 7 or changing an inclination angle of the ultrasound probe 6 as shown in FIG. 8, the area of the boundary surface within the intense ultrasonic wave passing region can be determined directly from the displayed ultrasound images, and used as the body surface passing area S in the calculation of the ultrasonic wave intensity $I_S$ at the body surface. Here, instead of utilizing the ultrasound diagnostic device as in the above embodiment, the MRI device or the CT device may be utilized to acquire the 3D images of the patient in obtaining the body surface passing area S.

Also, instead of the approximate calculation of the focal point peak ultrasonic wave intensity $I_P$ as in the embodiment described above, it is possible to obtain this focal point peak ultrasonic wave intensity $I_P$ easily by a simulation in which spherical waves that can be irradiated from a plurality of acoustic points assumed to be arranged at equal intervals on a piezoelectric transducer surface are superposed while taking the attenuation into account, so as to simulate the actual ultrasonic wave irradiation, for example. In this manner, the accurate intensity distribution can be obtained regardless of the shape of the piezoelectric transducer. Moreover, it is also possible to deal with the focal point scanning using the two dimensional array in this manner.

Also, instead of deriving conditions for the ultrasonic wave irradiation in a short time by ignoring the thermal conduction as in the embodiment described above, for the heating by the ultrasonic wave irradiation in an order of several seconds, it is also possible to simulate the heat generation in the living body more accurately by analytically solving the living body heat transport equation ignoring the blood flow term. (See, B. E. Billard, K Hynynen et al.: "Effects of Physical Parameters on High Temperature Ultrasound Hyperthermia" Ultrasound Med. Biol., Vol. 16, No. 4, pp. 409–420, 1990 for detail.) By using such a simulation, it becomes possible to conduct an accurate control of the irradiation time and power.

Furthermore, instead of moving the ultrasonic wave focal point by mechanically moving the entire applicator as in the embodiment described above, it is also possible to realize the focal point scanning by controlling the driving phases of a plurality of piezoelectric transducer elements in the phased array configuration as shown in FIG. 9. In this case, the ultrasonic energy density at the body surface and the focal point peak ultrasonic wave intensity can be calculated from the relative position of the applicator and the diseased portion within the patient and the phase control values of the piezoelectric transducer elements similarly as in the embodiment described above. In addition, it is also possible to store the pre-calculated values for the ultrasonic energy density at the body surface and the focal point peak ultrasonic wave intensity in a table memory, and carry out the optimum irradiation control as described above by reading out the necessary stored data from this table memory according to the phase control values of the piezoelectric transducer elements at the focal point depth with respect to the body surface.

It is to be noted that, besides those already mentioned above, many modifications and variations of the above embodiments may be made without departing from the novel and advantageous features of the present invention. Accordingly, all such modifications and variations are intended to be included within the scope of the appended claims.

What is claimed is:

1. An ultrasonic medical treatment apparatus, comprising:

an applicator having an ultrasonic wave generation source for irradiating ultrasonic waves to a treatment target portion within a body to be examined;

energy obtaining means for obtaining an ultrasonic energy of the ultrasonic waves irradiated at a tissue boundary surface of the body to be examined; and control means for controlling the applicator such that the ultrasonic energy at the tissue boundary surface obtained by the energy obtaining means becomes less than a prescribed threshold.

2. The apparatus of claim 1, wherein the control means uses the prescribed threshold which is determined in view of an influence on the tissue boundary surface due to the ultrasonic waves.

3. The apparatus of claim 2, wherein the control means uses the prescribed threshold which is determined as a limit for causing a damage on the tissue boundary surface due to heating by the ultrasonic waves.

4. The apparatus of claim 1, wherein the energy obtaining means obtains the ultrasonic energy of the ultrasonic waves irradiated at the tissue boundary surface which is a body surface of the body to be examined.

5. The apparatus of claim 1, wherein the control means controls the applicator by controlling at least one of a driving power and an ultrasonic wave irradiation time of the ultrasonic wave generation source in the applicator.

6. The apparatus of claim 1, wherein the tissue boundary surface is a body surface of the body to be examined, and the control means controls the applicator by controlling at least one of a driving power and an ultrasonic wave irradiation time of the ultrasonic wave generation source in the applicator to satisfy the following condition:

$$I_S \times t_S \times f < 124 \ [MHz \cdot J/cm^2]$$

where $I_S$ is an ultrasonic wave intensity at the body surface, $t_S$ is the ultrasonic wave irradiation time, and f is a frequency of the ultrasonic waves irradiated from the applicator.

7. The apparatus of claim 1, wherein the energy obtaining means calculates the ultrasonic energy irradiated at the tissue boundary surface according to a focusing level, a frequency, and a focal point depth with respect to the tissue boundary surface of the ultrasonic waves irradiated from the applicator.

8. The apparatus of claim 1, wherein the energy obtaining means also obtains an ultrasonic energy of the ultrasonic waves irradiated at a focal point of the ultrasonic waves, and the control means controls the applicator such that the ultrasonic energy at the tissue boundary surface obtained by the energy obtaining means becomes less than a first the prescribed threshold and the ultrasonic energy at the focal point obtained by the energy obtaining means becomes greater than another prescribed threshold.

9. The apparatus of claim 8, wherein the control means uses the prescribed threshold which is determined in view of an influence on the tissue boundary surface due to the ultrasonic waves and the another prescribed threshold which is determined in view of a medical treatment effect at the focal point due to the ultrasonic waves.

10. The apparatus of claim 9, wherein the control means uses the prescribed threshold which is determined as a limit for causing a damage on the tissue boundary surface due to heating by the ultrasonic waves, and the another prescribed threshold which is determined as a limit for achieving a sufficient medical treatment effect on the treatment target portion located at the focal point of the ultrasonic waves.

11. A method of ultrasonic medical treatment, comprising the steps of:

irradiating ultrasonic waves from an applicator having an ultrasonic wave generation source to a treatment target portion within a body to be examined;

obtaining an ultrasonic energy of the ultrasonic waves irradiated at a tissue boundary surface of the body to be examined; and controlling the applicator such that the ultrasonic energy at the tissue boundary surface obtained at the obtaining step becomes less than a prescribed threshold.

12. The method of claim 11, wherein the prescribed threshold is determined in view of an influence on the tissue boundary surface due to the ultrasonic waves.

13. The method of claim 12, wherein the prescribed threshold is determined as a limit for causing a damage on the tissue boundary surface due to heating by the ultrasonic waves.

14. The method of claim 11, wherein the tissue boundary surface is a body surface of the body to be examined.

15. The method of claim 11, wherein the controlling step controls the applicator by controlling at least one of a driving power and an ultrasonic wave irradiation time of the ultrasonic wave generation source in the applicator.

16. The method of claim 11, wherein the tissue boundary surface is a body surface of the body to be examined, and the controlling step controls the applicator by controlling at least one of a driving power and an ultrasonic wave irradiation time of the ultrasonic wave generation source in the applicator to satisfy the following condition:

$$I_S \times t_S \times f < 124 \ [MHz \cdot J/cm^2]$$

where $I_S$ is an ultrasonic wave intensity at the body surface, $t_S$ is the ultrasonic wave irradiation time, and f is a frequency of the ultrasonic waves irradiated from the applicator.

17. The method of claim 11, wherein the obtaining step calculates the ultrasonic energy irradiated at the tissue boundary surface according to a focusing level, a frequency, and a focal point depth with respect to the tissue boundary surface of the ultrasonic waves irradiated from the applicator.

18. The method of claim 11, wherein the obtaining step also obtains an ultrasonic energy of the ultrasonic waves irradiated at a focal point of the ultrasonic waves, and the controlling step controls the applicator such that the ultrasonic energy at the tissue boundary surface obtained at the obtaining step becomes less than the prescribed threshold and the ultrasonic energy at the focal point obtained at the obtaining step becomes greater than another prescribed threshold.

19. The method of claim 18, wherein the first prescribed threshold is determined in view of an influence on the tissue boundary surface due to the ultrasonic waves while the another prescribed threshold is determined in view of a medical treatment effect at the focal point due to the ultrasonic waves.

20. The method of claim 19, wherein the prescribed threshold is determined as a limit for causing a damage on the tissue boundary surface due to heating by the ultrasonic waves, while the another prescribed threshold is determined as a limit for achieving a sufficient medical treatment effect on the treatment target portion located at the focal point of the ultrasonic waves.

* * * * *